(12) United States Patent
Qiao et al.

(10) Patent No.: US 9,867,860 B2
(45) Date of Patent: Jan. 16, 2018

(54) FORMULATIONS FOR PREVENTING AND TREATING DECREASING PLATELET CELL COUNTS

(71) Applicants: Huihong Qiao, St Louis, MO (US); Wenjian Zhang, Beijing (CN)

(72) Inventors: Huihong Qiao, St Louis, MO (US); Wenjian Zhang, Beijing (CN)

( * ) Notice: Subject to any disclaimer, the term of this patent is extended or adjusted under 35 U.S.C. 154(b) by 716 days.

(21) Appl. No.: 14/325,688

(22) Filed: Jul. 8, 2014

(65) Prior Publication Data

US 2016/0008416 A1    Jan. 14, 2016

Related U.S. Application Data

(60) Provisional application No. 61/858,635, filed on Jul. 26, 2013.

(51) Int. Cl.

| | | |
|---|---|---|
| *A61K 36/185* | (2006.01) |
| *A61K 36/48* | (2006.01) |
| *A61K 45/06* | (2006.01) |
| *A23L 2/02* | (2006.01) |
| *A23L 33/105* | (2016.01) |
| *A23L 33/15* | (2016.01) |
| *A23L 33/155* | (2016.01) |
| *A61K 31/355* | (2006.01) |
| *A61K 31/375* | (2006.01) |
| *A61K 31/519* | (2006.01) |
| *A61K 31/592* | (2006.01) |
| *A61K 31/593* | (2006.01) |
| *A61K 31/714* | (2006.01) |
| *A61K 33/04* | (2006.01) |
| *A61K 33/26* | (2006.01) |

(52) U.S. Cl.
CPC .............. *A61K 36/48* (2013.01); *A23L 2/02* (2013.01); *A23L 33/105* (2016.08); *A23L 33/15* (2016.08); *A23L 33/155* (2016.08); *A61K 31/355* (2013.01); *A61K 31/375* (2013.01); *A61K 31/519* (2013.01); *A61K 31/592* (2013.01); *A61K 31/593* (2013.01); *A61K 31/714* (2013.01); *A61K 33/04* (2013.01); *A61K 33/26* (2013.01); *A61K 36/185* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 2007/0154575 A1* | 7/2007 | Shimoda | ............ | A61K 31/7008 424/756 |
| 2013/0196937 A1* | 8/2013 | Shimoda | ................ | A61K 8/602 514/27 |
| 2014/0065251 A1* | 3/2014 | Binachon | ............. | A61K 36/185 424/769 |

FOREIGN PATENT DOCUMENTS

| | | |
|---|---|---|
| CN | 200510051536 B2 | 4/2007 |
| CN | 200810232388 A1 | 4/2009 |
| CN | 101288703 B2 | 3/2011 |
| CN | 200810055637 B2 | 5/2011 |
| CN | 101199586 B2 | 12/2011 |
| CN | 102145063 B2 | 9/2012 |
| CN | 201210175352 A1 | 10/2012 |
| CN | 102283951 B2 | 1/2013 |
| WO | PCT/IN2008/000585 A1 | 4/2010 |
| WO | WO/2011/028098 A1 | 10/2011 |

* cited by examiner

*Primary Examiner* — Chris R Tate
(74) *Attorney, Agent, or Firm* — Huihong Qiao

(57) ABSTRACT

The invention provides formulations to prevent or treat decreasing platelet cell counts. The formulations essentially consist of peanut skins, papaya leaves, folic acid, vitamin B12, vitamin C, vitamin D, vitamin E, selenium, and iron. In some formulations, some vitamins are replaced by fruit or vegetable juice.

6 Claims, No Drawings

FORMULATIONS FOR PREVENTING AND TREATING DECREASING PLATELET CELL COUNTS

CROSS-REFERENCE TO RELATED APPLICATIONS

This application claims priority to a US Provisional Application No. 61/858,635, filed on Jul. 26, 2013, which is incorporated by reference herein in its entirety.

FIELD OF THE INVENTION

The present invention relates to dietary supplements. More particularly, dietary supplements formulated to prevent or treat decreasing platelet cell counts under various conditions. In other words, the invented dietary supplements formulated to prevent or treat thrombocytopenia, which is defined as platelet counts <150,000/ml.

BACKGROUND OF THE INVENTION

The invention is directed to formulations that are able to prevent or treat decreasing platelet cell counts.

Platelets are small cytoplasmic bodies derived from megakaryocytes. They are also called thrombocytes. Platelets are produced in blood cell formation (thrombopoiesis) in bone marrow, by budding off from megakaryocytes. The platelet count in the circulating blood of a healthy person is typically between $150 \cdot 10^9$ and $400 \cdot 10^9$ per liter of blood. Newborn babies have a slightly lower level, but are normally within the adult range by three months of age (Thon et al., 2010; Malara et al., 2012).

Platelets are important for hemostasis. Upon vascular injury, platelets instantly adhere to the exposed extracellular matrix resulting in platelet activation and aggregation to form a hemostatic plug (Id.). However, platelets mis-function caused serious problems. Platelets aggregation may lead thrombosis, consequently, leads to atherosclerosis or stroke [Siddiqui et al., ISSN (Online): 1875-533X]. Platelets aggregation is also contribute to cancer metastasis (Reymond et al., 2013).

A low platelet count is a common problem and has serious consequence. A platelet count of less than 150,000/mL is defined as thrombocytopenia. Thrombocytopenia is a common reason for a hematology consult in both the inpatient and outpatient setting (Wong et al, 2012). Thrombocytopenia is encountered across a number of conditions, including immune (idiopathic) thrombocytopenic purpura (ITP), myelodysplastic syndromes (MDS), liver cirrhosis, aplastic anemia, human immunodeficiency virus (HIV) infection, and major cardiac surgery, as well as a host of relevant genetic disorders. Cancer treatments, such as radiation or chemotherapy, also cause thrombocytopenia. The incidence of chemotherapy-induced thrombocytopenia is 21.8%, with the highest frequency seen in patients receiving carboplatin alone or in combination (Id.). Chemotherapy-induced thrombocytopenia often leads to a reduction in chemotherapy, either a postponement or a reduction in the dose or number of chemotherapy cycles. This reduction has serious consequences: when chemotherapy dose was decreased to less than 85% of the target dose in breast cancer patients, overall and relapse-free survival were significantly decreased (Vadhan-Raj S, 2009).

Thrombocytopenia is difficult to manage in the clinic and the consequences can be life threatening (Connell N T, 2012). The most common treatment of thrombocytopenia is platelet transfusion. Platelet transfusions total well over 10 million units per year in the United States, which present a great burden to the US blood community. Platelet transfusion carries the risk of infection, and can be low efficacy due to allo-immunization. Moreover, platelet transfusion is possibly associated with a decrease in the long-term survival of acute leukemia patients because it is possible that it increases the risk of chemoresistant relapse (Rioux-Masse B et al., 2012) Among the cytokines that play a significant role in megakaryopoiesis, IL-11 and thromobopoietin (TPO) have been shown to stimulate megakaryocyte maturation (Broudy V C et al., 1995; Teramura M et al., 1992). Clinical studies have demonstrated that recombinant human IL-11 could correct thrombocytopenia associated with chemotherapy, HCV infection, or early liver cirrhosis in some degree. In randomized, placebo-controlled trial in patients with solid tumors who had previously received platelet transfusion because of myelosuppression, IL-11 reduced the number of patients in need of platelet transfusions by 26%. However, the side effects of rhIL-11 are significant, including edema in more than 50% of patients, dyspnea, atrial arrhythmias, syncope, and fatigue (Tepler I et al., 1996; Fontana V et al., 2008; Ustun C et al., 2002). First generation of thrombopoietic agents were discontinued due to auto-reactive anti-TPO antibodies. TPO-receptor agonists, Romiplostim and Eltrombopag, have shown to increase platelet count in patients with ITP and liver disease. The two drugs require continuous treatments. Romiplostim costs $55,250 per patient per year. Eltrombopag must be taken every day apart from specific meals containing high levels of calcium (for example, milk), which leads to problems with compliance. The side effects are bone marrow fibrosis, thrombosis, and ocular toxicities (Kuter D J et al., 2008; Khellaf M et al., 2011; Bussel J B et al., Kuter D J et al., 2009; Zeng Y et al., 2011). The effect of TPO-receptor agonists in treating chemotherapy-induced thrombocytopenia is inconclusive (Basciano P A et al., 2012). A recent phase II study has shown that Eltrombopag failed to meet primary endpoint in patients receiving chemotherapy for advanced solid tumors due to slow therapeutic response (Kellam A et al., 2010).

DETAILED DESCRIPTION OF THE INVENTION

As explained above, development of new solutions for thrombocytopenia is still required for the above treatments are associated with high cost, side effects, potential risk, and unsatisfied efficacy.

The present invention provides solutions to prevent and treat thrombocytopenia. The invention includes ingredients that are effective in raising platelet counts, and vitamins and minerals that involves in platelets production.

The present invention is for a mammal, for instance a human.

The present invention provides dietary supplement formulations. Each formulation comprises active ingredients from two or three of the followings: herbs; vitamins, and minerals. Each formulation also includes one or more inactive ingredients, such as water, auxiliary agents, preservatives, etc.

The herbs can be in the form of herb extracts or herbs. The herbs are selected from a group essentially consisting of peanut skins, papaya leaves, Millettla, Polygonum cuspidatum, Agrimony, Eclipta, and Licorice.

Vitamins are selected from a group essentially consisting of folic acid, vitamin B12, vitamin C, vitamin D, and vitamin E.

Minerals comprise one or more minerals selected from a group essentially consisting of selenium and iron.

I. Active Ingredients

1. Herbs

A. Papaya Leaves

One active ingredient is dried papaya leaves extract. Papaya leaves are used by traditional medicine in Southeast Asia to treat thrombocytopenia caused by Dengue Fever. Clinical study showed that orally ingest of fresh juice from papaya leaves significantly increased platelet counts within 40 hours of administration. The juice induced ALox12 and PTAFR genes expression. The genes are associated to megakaryocyte production. Platelet counts increased rapidly in mice receiving dried papaya leaves extract (Subenthiran S et al., 2013).

Pre-clinical study showed that papaya leaves exhibit anti-tumor activities. Aqueous extract from dried leaves inhibited proliferation responses of various tumor cell lines, such as liver, lung, pancreatic, mesothelioma, lymphoma, and leukemia etc. The extract also enhanced cytoxicity of pre-activated peripheral blood mononuclear cells. Moreover, the extract up-regulated immunomodulatory genes (CCL2, CCL7, CCL8, SERINB2). Furthermore, the extract reduced Th2 type cytokine (IL-4) expression, but increased expression of Th1 type cytokines, such as IL-12, IFN-γ, and TNF-α. (Halim S Z, 2011).

B. Peanut Skins

While peanut skins are generally discarded as waste in food processing, they are used to prevent and treat chronic hemorrhage in Traditional Chinese Medicine (TCM) (Takano F, 2007). TCM contends that the effects of peanut skins include replenishing blood, stopping bleeding, dissolving clotting. Peanut skins are able to stop bleeding but not cause thrombosis. TCM uses peanut skins to treat hemorrhage caused by various diseases, such as immune thrombocytopenia, liver diseases, and chemotherapy, etc. The effectiveness of peanut skins in treatment of thrombocytopenia has been extensively studied in China. The first known paper was published in 1954 (Yao G Y, 2004). The most recent clinical study was published in 2012 (Wang 2012). Preclinical study showed that peanut skins extract was able to stop bleeding, contract vessels and reduce capillary permeability (Yao G Y, 2004). Clinical studies have tested the effectiveness of peanut skins in treatment of thrombocytopenia. In these clinical studies, peanut skins were applied alone or in a formula with other herbs.

Peanut skins are used in herbal formulations to raise platelets in immune thrombocytopenia patients. One clinical study reported that bleeding symptoms disappeared in 30 patients among the 38 immune thrombocytopenia patients treated by peanut skins and Sanqi (Chen G X, 2002).

Peanut skins are used to raise platelets in thrombocytopenia patients caused by liver cirrhosis. Cirrhosis may lead to splenomegaly, consequently, increased splenic sequestration leads to thrombocytopenia. One clinical study reported the effectiveness of peanut skins in treatment of thrombocytopenia among 28 liver cirrhosis patients. Platelet counts in each patient was <50,000/ml before treatment. Peanut skins aqueous extract was made by boiling and concentrating the extract. Patients drunk the aqueous extract from 30 grams peanut skins and 60 grams of peanut stems and leaves, once a day, for seven days. Platelet counts increased 30% in 26 out of 28 patients (92.9%). Epistaxis (nosebleed) disappeared in 85.7% patients. Gum bleeding disappeared in 89.2% patients (Zhao Y, 2005).

Peanut skins are used to raise platelets in chemotherapy-induced thrombocytopenia. One random controlled trial studied the efficacy and safety of peanut skins aqueous extract in raising platelets in patients receiving chemotherapy for solid tumors. 101 patients were randomly assigned to control group and treatment group. No statistic difference existed between the two groups of patients as to sex, age, tumor types, and chemotherapy treatments before administrating peanut skins extract. The treatment group received the aqueous extract from 10 grams peanut skins per day, for seven days. Three patients in the treatment group were out of the study because of nausea and vomit. During the study, two patients needed platelet transfusion in the control group; no patients needed platelet transfusion in the treatment group. Thrombocytopenia in patients of treatment group was significantly less severe than that in the control group. (See Table 1) (Wang Y, 2012).

TABLE 1

Comparison of thrombocytopenia between the control group and treatment group. N: patient number. 0: platelet counts >100 × $10^9$/L. I: (75~99) × $10^9$/L. II: (50~74) × $10^9$/L. III: 25~49) × $10^9$/L. IV ≤25 × $10^9$/L.
Comparison of thrombocytopenia in the two groups of patients

| Group | n | 0 | I | II | III | IV |
|---|---|---|---|---|---|---|
| Treatment | 48 | 14 | 22 | 4 | 6 | 2 |
| Control | 50 | 7 | 15 | 10 | 10 | 8 |

$X^2 = 10.793$,
$p = 0.029$

Another randomly controlled trial also showed that peanut skins is effective in maintain platelet counts within normal range. In the study, a formula combined peanut skins and other herbs were tested to combat the side effects of Gemcitabine, such as leukopenia, thrombocytopenia, anemia, and digestive tract problems. The role of peanut skins in the formula is to raise platelet counts. 42 patients were randomly divided into groups. There was no significant difference between the two groups as to age, sex, pathological stages, and quality of life before treatment. Gemcitabine was administrated 1000 mg/$m^2$ intravenously on d1 and d8 through a 21-day cycle. The formulation contains 10 grams peanut skins Aqueous extract of the formulation was given orally twice a day through a cycle. The effectiveness was evaluated at the end of two cycles. Significantly more patients in the peanut skins formulation group had platelet counts in the normal range. (Table 2) (Gong J Y, 2012).

TABLE 2

Comparison of hemogram after two cycles of treatment. Abbreviation: Treat: the group of patients was given peanut skins soup. Con: the group with no peanut skins treatment. WBC: white blood cell counts. HB: hemoglobin counts. PLT: platelet counts. 0: platelet counts >100 × $10^9$/L. I: (75~99) × $10^9$/L. II: (50~74) × $10^9$/L. III: 25~49) × $10^9$/L. IV ≤25 × $10^9$/L.
Comparison of Hemogram

| Group | cases | WBC | | | | | HB | | | | | PLT | | | | |
|---|---|---|---|---|---|---|---|---|---|---|---|---|---|---|---|---|
| | | 0 | I | II | III | IV | 0 | I | II | III | IV | 0 | I | II | III | IV |
| Treat | 21 | 3 | 3 | 4 | 6 | 5 | 10* | 9 | 11 | 0 | 1 | 14* | 5 | 1 | 1 | 0 |
| Con | 21 | 4 | 2 | 3 | 7 | 5 | 5 | 8 | 5 | 2 | 1 | 6 | 9 | 4 | 0 | 2 |

*P < 0.05

One pre-clinical study compared the effectiveness of peanut skins with recombinant IL-11 on raising platelet counts in myelosuppressed mice. Mice were intraperitoneally injected 75 mg/Kg carboplatin for three consecutive days (d1, d2, d3). From d4, mice were gavage fed with peanut skins aqueous extract or subcutaneously administrated rhIL-11 for seven days. Platelets were counted on d7 and d10. On d7, IL-11 and peanut skins extract (10 g/Kg) significantly improved platelet counts comparing with the control thrombocytopenia group. However, the counts were significantly higher in the IL-11 group than that in the peanut skins extract group. On d10, IL-11, and peanut skins extract (10 g/Kg and 5 g/Kg) further improved platelet counts. The counts in the IL-11 and peanut skins extract 10 g/Kg groups had no statistic difference. The above results indicated that peanut skins aqueous extract is effective in raising platelet counts in thrombocytopenia mice. However, the response is slower comparing with recombinant IL-11 (Wang, 2010).

In summary, pre-clinical and clinical studies have indicated that peanut skins and papaya leaves are safe and effective in raising platelet counts under various conditions. The response to peanut skins seems slow. However, papaya leaves significantly raised platelets with in 40 hours of administration. A formula composited with the two herbs should synergize the effectiveness of the two.

C. Other Herbs

Millettla, Polygonum cuspidatum, Agrimony, and Eclipta have been used in Chinese Medicine formulations to raise platelet cell counts. Licorice is used to reduce side effects in Chinese Medicine formulations.

2. Vitamins and Minerals

Vitamins and minerals are indispensible in hematopoiesis. The vitamins and minerals compositions of the present invention comprise one or more minerals selected from a group essentially consisting of folic acid, vitamin B12, vitamin C, vitamin E, vitamin D, selenium, and Iron.

Vitamin B12 and folate deficiency cause megaloblastosis and pancytopenia through inhibition of purine synthesis. Thrombocytopenia may be the predominant cytopenia, and can be severe. (Wong, 2012) Primary and secondary folate and vitamin B12 deficiency caused thrombocytopenia were observed in both human and experimental animals. Folate and vitamin B12 deficiency cause hemolysis, elevated liver enzymes and low platelets syndrome during pregnancy. (Hartong, 2007). Repletion of Vitamin B12 and folate rapidly corrects the thrombocytopenia (Wong, 2012).

The platelet count and platelet turnover were greatly decreased by Vitamin E or selenium deficiency in young pigs. With selenium deficiency, the prothrombin time was shortened. The survival of platelets labeled with $^{75}$Se-selenomethionine and the percent isotope incorporated into platelets were reduced in association with vitamin E deficiency (Fontaine, 1977).

Even though there is no direct evidence that vitamin D is required in platelet production, vitamin D receptor is expressed on various hematopoietic precursors as well as monocytes, and some thymocytes (Hall, 2013). Dr. Bockow and Dr. Kaplan reported two cases of refractory immune thrombocytopenia were successfully treated with high-dose vitamin D supplementation and hydroxychloroquine (Bockow, 2013). In addition, vitamin D is effective in prevention of various cancers and beneficial in therapy for hematological malignancies (Hall, 2013).

Iron may be including in the formulas because peanut skins also stimulate red blood cell production. Iron is an essential element for blood production. Vitamin C improves iron absorption by keeps it in the ferrous form. Vitamin C also regenerates vitamin E (Niki, 1987).

II. Substitute Ingredients

Vitamins and minerals used herein can be substituted by fruit or vegetable juice concentration and brown sugar, those of which are rich in vitamins and minerals. However, Vitamin B12 and vitamin D have to be supplemented because none of the above is rich of vitamin B12 and vitamin D.

Fruits or vegetables rich in vitamins and minerals needed in the formulations are, but not limited to, mango, orange, papaya, pineapple, pomegranate, raspberries, strawberries, blackberries, blueberries, cranberries, kiwi, peach, avocado, cherries, dates, figs, grapes, spinach, peas, and asparagus.

III. Auxiliary Agent

The formulations of the present invention may also contains at least one of any suitable auxiliary such as, but not limited to, diluent, binder, stabilizer, buffers, salts, lipophilic solvents, preservative or the like. Pharmaceutically acceptable auxiliaries are preferred. Examples and methods of preparing such sterile solutions are well known in the art and can be found in well-known texts such as, but not limited to, REMINGTON'S PHARMACEUTICAL SCIENCES (Gennaro, Ed., 18th Edition, Mack Publishing Co. (1990)). Pharmaceutically acceptable carriers can be routinely selected that are suitable for the mode of administration, solubility and/or stability of the compound.

IV. Other Ingredients

Other ingredients include, but not limited to, acceptable preservatives for pharmaceutical or food industry.

V. Daily Dosage and Preparation of Active Ingredients

The formulations are intended to be taken twice or three times a day. Dosage here refers to daily dosage.

1) Dosage and Preparation of Herbs

A. Dosage of Herbs

Dosage of herbs varies in the clinical studies. For the convenience, dry herbs used in this invention presents a range of 0.01 to 120 grams, preferably 5 to 30 grams, daily. If fresh herbs were used, preferably 10 to 60 grams.

B. Preparation of Herbs

Preparation of herbs can be achieved by traditional methods, such as boiling, distilling etc., or modern technology, such as exemplified in Nanometer Haemostatic Medication and Methods of Preparation (CN 1364542A).

2) Daily Dosage of Vitamins and Minerals

The dosage of folic acid described herein preferably 30 mcg to 1000 mcg, more preferably 200 mcg to 800 mcg.

The term "vitamin B12" refers to all forms of cobalamin including, but not limited to, hydroxocobalamin, cyanocobalamin and methylcobalamin. The dose of vitamin B12 described herein preferably 0.4 mcg to 1000 mcg, and more preferably 0.6 mcg to 1.2 mcg.

The term "vitamin C" is used herein to refer to any form of vitamin C including ascorbate and L thronate. The does of vitamin C described herein preferably 20 mg to 2000 mg, and more preferably 20 mg to 100 mg.

The term "vitamin D" is used to refer to both cholecalciferol (vitamin D3) and ergocalciferol (vitamin D2). In a preferred embodiment, the vitamin D is also including calcium carbonate, phosphate, lactate, gluconate, citrate and combinations thereof. The does of vitamin D described herein preferably 200 IU to 4000 IU.

The term "vitamin E" refers both the fat-soluble form and water-solublized form. The dose range is preferably 6 IU to 1,100 IU), more preferably 15 IU to 50 IU.

The term "iron" is used herein to refer to any form of iron including gluconate, sulfate, chloride, elemental and fumarate. The does of iron described herein preferably 0.27 mg to 45 mg, and more preferably 8 mg to 18 mg.

The term "selenium" is used herein to refer to both the inorganic (selenate and selenite) and organic forms (selenomethionine and selenocysteine), preferably selenomethionine. The does of selenium described herein preferably 7.5 mcg to 400 mcg, and more preferably 15 mcg to 45 mcg.

VII. The Make of Tablets, Capsules, Soft-Gels, Syrup or Juice

The present invention may be made into tablets, capsules, soft-gels, syrup or juice in accordance with well-known methods and procedures of the pharmaceutical or food industry.

VIII. Examples

The doses in the examples are for 5 days.

Example 1: Peanut Skins Tablets or Capsules

Add 100 grams peanut skins to 1000 ml water, boil the peanut skins and simmer for more than half an hour. Then, filter and pour liquid into a sterilized container. Concentrate and cool the extract, then add folic acid 2000 mcg; vitamin B12 12 mcg; vitamin D 3000 IU; vitamin E 112 IU; selenium 275 mcg; All of the above ingredients is to be made into 20 to 30 tablets or capsules in accordance with the pharmaceutical best mode.

Example 2: Peanut Skins Syrup

Prepare peanut skins extract and add vitamins and selenium as in example 1, then add sugar or other flavor addictives, and distilled-water to a final volume of 150 ml.

Example 3: Papaya Leave Tablets or Capsules

The extract from 150 grams dried papaya leaves is made as in example 1, then mix with folic acid 2000 mcg; vitamin B12 12 mcg; vitamin D 3000 IU; vitamin E 112 IU; selenium 275 mcg; All of the above ingredients is to be made into 20 to 30 tablets or capsules in accordance with the pharmaceutical best mode.

Example 4: Papaya Leave Syrup

Prepare extract from 150 grams papaya leave, mix with vitamins and selenium as in example 1, then add sugar or other flavor addictives, and distilled-water to a final volume of 150 ml.

Example 5: Peanut Skins and Papaya Leave Tablets or Capsules

Prepare aqueous extract from 100 grams of peanut skins and 150 grams of dried papaya leave as in example 1. Then mix with vitamins and selenium as in example 1. All of the above ingredients are to be made into 20 tablets or capsules in accordance with the pharmaceutical best mode.

Example 6: Peanut Skins and Papaya Leave Syrup

Prepare active ingredients as in example 5, add sugar or other flavor addictives, and distilled-water to a final volume of 150 ml.

VIII. Administration

The present invention provides solutions to prevent or treat decreasing platelet cell counts. The formulations can be administrated before or after platelet counts begin to drop. A mammal may take two to four tablets twice or three times per day. The juices are to be taken 15 ml per time, twice or three times a day.

IX. Disclaimer

It also should be appreciated by those skilled in the art that the specific embodiments disclosed above may be readily utilized as a basis for modifying or designing other formulations for carrying out the same purposes of the present invention. It should also realized by those skilled in the art that such equivalent formulations do not depart from the spirit and scope of the invention as set forth in the appended claims.

REFERENCES

Wong E Y, Rose M G, Why Does My Patient Have Thrombocytopenia? Hematol Oncol Clin N Am 26: 231-252 (2012).

Thon J N, Italiano J E, Platelet Formation. Semin Hematol, 47(3): 220-226 (2010). Malara A, Balduini A, Blood Platelet Production and Morphology. Thrombosis Research 129: 241-244 (2012).

Siddiqui T I, A. Kumar K. S. and Dikshit D K, Platelets and Atherothrombosis: Causes, Targets and Treatments for Thrombosis. Current Medicinal Chemistry, vol 20: 2779-2797, ISSN (Online): 1875-533X.

Reymond A, d'Agua B B, Ridley A, Crossing the Endothelial Barrier during Metastasis. Nature Reviews Cancer 13, 858-870 (2013).

Vadhan-Raj S, Management of Chemotherapy-Induced Thrombocytopenia: Current Status of Thrombopoietic Agents. Seminars in Hematology Vol 46 (1), Suppl 2, S26-S32 (2009).

Connell N T, Sweeney J D. Does my patient have a life- or limb-threatening thrombocytopenia? Hematol Oncol Clin N Am 2012; 26:369-382.

Rioux-Masse B, Laroche V, Bowman R J, at el. The Influence of bleeding on trigger changes for platelet transfusion in patients with chemothereapy-induced thrombocytopenia. Transfusion 2012; June 7: 1-7.

Broudy V C, Lin N L, Kaushansky K. Thrombopoietin (c-mpl ligand) acts synergistically with erythropoietin, stem cell factor, and interleukin-11 to enhance murine megakaryocyte colony growth and increases megakaryocyte ploidy in vitro. Blood 1995; 85:1719-26.

Teramura M, Kobayashi S, Hoshino S, Oshimi K, Mizoguchi H. Interleukin-11 enhances human megakaryocytopoiesis in vitro. Blood 1992; 79:327-31.

Tepler I, Elias L, Smith J W, Hussein M, Rosen G, ChangAY, et al. A randomized placebo-controlled trial of recombinant human interleukin-11 in cancer patients with severe thrombocytopenia due to chemotherapy. Blood 1996; 87:3607-14.

Fontana V, Dudkiewicz P, Jy W, et al. Interleukin-11 for treatment of hepatitis C-associated ITP. Acta Haematol 2008; 119:126-32.

Ustun C, Dainer P M, Faguet G B. interleukin-11 administration normalizes the platelet count in a hypersplenic cirrhotic patient. Ann Hematol 2002; 81:609-610.

Kuter D J, Bussel J B, Lyons R M, et al. Efficacy of romiplostim in patients with chronic immune thrombocytopenic purpura: a double-blind randomized controlled trial. Lancet 2008; 371:395-403.

Khellaf M, Michel M, Quittet P, et al. Romiplostim safety and efficacy for immune thrombocytopenia in clinical practice: 2-year results of 72 adults in a romiplostim compassionate-use program. Blood 2011; 118:4338-4345.

Bussel J B, Kuter D J, Pullarkat V, et al. Safety and efficacy of long-term treatment with romiplostim in thrombocytopenic patients with chronic ITP. Blood 2009; 113:2161-2171.

Zeng Y, Duan X, Xu J, Ni X. TPO receptor agonist for chronic idiopathic thrombocytopenic purpua. Cochrane Database Syst Rev 2011; 7: CD008235.

Basciano P A, Bussel J. Thrombopoietin-receptor agonists. Curr Opin Hematol 2012; 19:392-398.

Kellam A, Jagiello-Gruszfeld A, Bondarenko I N, et al. A randomized, double-blind, placebo-controlled, dose ranging study to assess the efficacy and safety of eltrombopag in patients receiving carboplatin/paclitaxel for advanced solid tumors. Current Medical Research & Opinion 2010; 26(10):2339-2346.

Subenthiran S, Choon T C, Cheong K C, et al., Carica Papaya Leaves Juice Significantly Accelerates the Rate of Increase in Platelet Count among Patients with Dengue Fever and Dengue Haemorrhagic Fever. Evidence-Based Complementary and Alternative Medicine, Volume 2013, Article ID 616737.

Halim S Z, Abdullah N R, Afzan A, et al., Acute Toxicity Study of Carica Papaya Leaf Extract in Sprague Dawley Rats. Journal of Medicinal Plants Research 5(xx), 1867-1872, (2011).

Takano F, Takata T, Yoshihara A, et al. Aqueous extract of peanut skin and its main constituent procyanidin A1 suppress serum IgE and IgG1 levels in mice-immunized with Ovalbumin. Biol. Pharm. Bull. 2007; 30(5):922-927.

Yao G Y, Xie B Z. Modern pharmacology and clinic of Chinese Traditional Medicine. P693-694. 2004.

Wang Y, Wu H L, Zhang Y J, Peanut Skin Aqueous Extract Prevent and Treat Chemotherapy-induced Thrombocytopenia 48 cases. Fujian Journal of TCM 43(5): 40-41, (2012).

Chen G X, Clinical Observation on effects of Peanut Skin and Sanqi treating IPT 38 cases. Yunnan TCM Journal 23(5): 13-14, (2002).

Zhao Y, Peanut Skin with Stem and Leaves treated liver cirrhosis 24 cases. Chinese Archives of TCM 23(10): 1917, 2005.

Gong J Y, Clinical Observation of Ejiao Peanut Skin Combined Gemcitabine in Treatment of Elderly Patients with Advanced Central Non-small Cell Lung Cancer. Hubei Journal of TCM 34(11): 8-10, (2012).

Wang C X, Peanut Skin Aqueous Extract Treats Chemotherapy-induced Thrombocytopenia in Mice. (Xianxi TCM University, Graduation Thesis, 20100401).

Hartong S. C. C., European Journal of Obstetrics & Gynecology and Reproductive Biology 131: 235-245, (2007).

Fontaine M, Valli V E O, Young L G, Studies on Vitamin E and Selenium Deficiency in Young Pigs IV. Effect on Coagulation System. Can J. Comp. Med. 41: 64-76, (1977).

Bockow B, Kaplan T B, Refractory Immune Thrombocytopenia Successfully Treated with High-dose Vitamin D Supplementation and Hydroxychloroquine: Two Case Reports. Journal of Medical Case Reports 7:91, (2013).

Hall A C, Juckett M B, The Role of Vitamin D in Hematologic Disease and Stem Cell Transplantation. Nutrients 5, 2206-2221, (2013).

Etsuo NIKI, Interaction of Ascorbate and α-Tocopherol Annals of the New York Academy of Sciences, Vol 498, Third Conference on Vitamin C 186-199, (1987).

What claimed is:

1. A composition for preventing or treating thrombocytopenia, comprising effective amounts of vitamin D, vitamin E, selenium, and an aqueous extract of peanut skins or an aqueous extract of papaya leaves, wherein the composition is in the form of a tablet or a capsule.

2. The composition according to claim 1, wherein the composition further comprises one or more vitamins selected from the group consisting of folic acid, vitamin B12, and vitamin C.

3. The composition according to claim 1, wherein the composition further comprises iron.

4. A composition for preventing or treating thrombocytopenia, comprising effective amounts of vitamin D, vitamin E, selenium, an aqueous extract of peanut skins and an aqueous extract of papaya leaves, wherein the composition is in the form of a tablet or capsule.

5. The composition according to claim 4, wherein the composition further comprises one or more vitamins selected from a group consisting of folic acid, vitamin B12, and vitamin C.

6. The composition according to claim 4, wherein the composition further comprises iron.

* * * * *